United States Patent
Bhatia et al.

(10) Patent No.: US 10,698,981 B2
(45) Date of Patent: Jun. 30, 2020

(54) AUTOMATIC DETECTION OF MEDICAL IMAGE ACQUISITION PROTOCOL

(71) Applicants: Parmeet Singh Bhatia, Frazer, PA (US); Amit Kale, Bangalore (IN)

(72) Inventors: Parmeet Singh Bhatia, Frazer, PA (US); Amit Kale, Bangalore (IN)

(73) Assignee: Siemens Healthcare GmbH, Erlangen (DE)

(*) Notice: Subject to any disclaimer, the term of this patent is extended or adjusted under 35 U.S.C. 154(b) by 141 days.

(21) Appl. No.: 15/387,783

(22) Filed: Dec. 22, 2016

(65) Prior Publication Data
US 2017/0185713 A1 Jun. 29, 2017

(30) Foreign Application Priority Data
Dec. 24, 2015 (IN) .......................... 1336/KOL/2015

(51) Int. Cl.
*G06F 19/00* (2018.01)
*G06K 9/00* (2006.01)
(Continued)

(52) U.S. Cl.
CPC .............. *G06F 19/321* (2013.01); *G06K 9/00* (2013.01); *G06T 7/0012* (2013.01);
(Continued)

(58) Field of Classification Search
CPC ......... G06F 19/321; G06T 2207/30204; G06T 7/0012
See application file for complete search history.

(56) References Cited

U.S. PATENT DOCUMENTS 6,912,061 B1* 6/2005 Ozaki ................ H04N 1/00641
358/1.15
7,072,498 B1* 7/2006 Roehrig ................ G06T 7/0012
378/28
(Continued)

FOREIGN PATENT DOCUMENTS

CN 101295309 A 10/2008
CN 103473569 A 12/2013
(Continued)

OTHER PUBLICATIONS

Kalpathy-Cramer, Jayashree et al., "Effectiveness of Global Features for Automatic Medical Image Classification and Retrieval—the experiences of OHSU at ImageCLEFmed", Pattern Recognit Lett. Nov. 1, 2008; 29(15): 2032-2038 (Year: 2008).*
(Continued)

*Primary Examiner* — Gandhi Thirugnanam
(74) *Attorney, Agent, or Firm* — Lempia Summerfield Katz LLC

(57) ABSTRACT

The disclosure relates to method and device for determining at least a portion of an anatomy from a set of medical images. Thereafter, the image acquisition protocol associated with the medical images is determined automatically based on the determined anatomy. The image acquisition protocol is automatically determined by extracting one or more features associated with the medical images characterizing the acquisition protocol. Thereafter, the medical images are classified based in the features. Further, the medical images are assigned with an acquisition protocol label based on the classification of the medical images. The medical images are displayed with the respective protocol labels. Further, medical images acquired with an identified image acquisition protocol at different time instances are displayed for comparative analysis.

16 Claims, 2 Drawing Sheets

(51) Int. Cl.
   *G06T 7/00*    (2017.01)
   *G06K 9/46*    (2006.01)
   *G06K 9/62*    (2006.01)

(52) U.S. Cl.
   CPC ... *G06K 9/6284* (2013.01); *G06K 2009/4666* (2013.01); *G06K 2209/05* (2013.01); *G06T 2207/10088* (2013.01); *G06T 2207/30204* (2013.01); *G06T 2210/41* (2013.01)

(56) References Cited

U.S. PATENT DOCUMENTS

| | | | |
|---|---|---|---|
| 9,092,672 B1 | 7/2015 | Felch | |
| 2006/0008130 A1* | 1/2006 | Yamamichi | H04N 1/00631 382/128 |
| 2007/0064981 A1* | 3/2007 | Meijer | G06F 19/321 382/128 |
| 2008/0095418 A1* | 4/2008 | Moriya | A61B 6/563 382/128 |
| 2008/0123918 A1* | 5/2008 | Saotome | G06T 5/009 382/128 |
| 2008/0215630 A1* | 9/2008 | Oosawa | G06F 19/321 |
| 2009/0287505 A1* | 11/2009 | Wood | G06Q 50/22 705/3 |
| 2014/0016846 A1* | 1/2014 | Blaskovics | A61B 5/055 382/131 |
| 2014/0222444 A1* | 8/2014 | Cerello | G06Q 10/00 705/2 |
| 2015/0025909 A1* | 1/2015 | Hayter, II | G06F 19/321 705/3 |
| 2015/0278442 A1* | 10/2015 | Rezaee | G06F 19/321 382/128 |
| 2015/0278444 A1* | 10/2015 | Westin | G06F 21/602 382/128 |
| 2017/0185713 A1* | 6/2017 | Bhatia | G06F 19/321 |

FOREIGN PATENT DOCUMENTS

| | | |
|---|---|---|
| CN | 103536305 A | 1/2014 |
| JP | 2006006790 A | 1/2006 |

OTHER PUBLICATIONS

J. Kalpathy-Cramer and William Hersh, "Automatic Image Modality Based Classification and Annotation to Improve Medical Image Retrieval", Studies in Health Technology and Informatics 129 (2007) 1334-1338 (Year: 2007).*

Achanta, Radhakrishna, et al. "Frequency-tuned salient region detection." Computer vision and pattern recognition, 2009. cvpr 2009. ieee conference on. IEEE, 2009.

Ojala, Timo, Matti Pietikainen, and Topi Maenpaa. "Multiresolution gray-scale and rotation invariant texture classification with local binary patterns" IEEE Transactions on pattern analysis and machine intelligence 24.7 (2002).

Briassouli, Alexia; "Health Monitoring and Personalized Feedback using Multimedia Data" Springer Verlag; pp. 74-91; 2015.

Bui, Alex; "Medical Imaging Informatics"; Springer Verlag. pp. 252-255; 2010.

Kagadis George C.; "Informatics in Medical Imaging" CRC; pp. 258; XP055371821; 2012.

Mueler Henning; "ImageCLEF Experimental Evaluation in Visual Information Retrieval" Springer Verlag. pp. 403-405; 2010.

Chinese Office Action and Search Report for Chinese Application No. 201611205952.2 dated Nov. 20, 2019.

\* cited by examiner

US 10,698,981 B2

AUTOMATIC DETECTION OF MEDICAL IMAGE ACQUISITION PROTOCOL

The application claims the benefit of Indian Patent Application No. 1336/KOL/2015, filed Dec. 24, 2015, which is hereby incorporated by reference in its entirety.

TECHNICAL FIELD

This disclosure relates to a method and system for automatic detection of medical imaging acquisition protocol using image analytics and machine learning.

BACKGROUND

Today the medical imaging technology is advancing rapidly. Medical images of patients are being capture using technologies such as x-rays, ultrasound computerized tomography (CT) scans, magnetic resonance (MR) imaging, nuclear medicine (NM) imaging, positron emission computed tomography (PET), etc., to be electronically acquired, stored, retrieved, displayed, and transmitted for viewing by medical personnel. The acronym, PACS (Picture Archiving and Communication System), is an industry term for an integrated system of equipment and software that permits radiographic images, such as x-rays, ultrasound computerized tomography (CT) scans, magnetic resonance (MR) imaging, nuclear medicine (NM) imaging, positron emission computed tomography (PET), etc., to be electronically acquired, stored, retrieved, displayed, and transmitted for viewing by medical personnel. The PACS system may include an interface, which is a software application, which aids in accessing and retrieval of images stored in the PACS database. The queries received for a set of images are matched by DICOM header of the images stored in the PACS.

The Digital Imaging and Communication in Medicine (DICOM) standard describes a file format for media storage and image distributions. The standard was created by the National Electrical Manufacturers Association (NEMA) to aid the distribution and viewing of medical images, such as CT scans, MEDICALIs, and ultrasound. The DICOM format includes a header portion and an image data portion.

The DICOM format uses a series of pre-defined tags and allows the definition of new tags, which may or may not be present for a given dataset. This flexibility is one of the features that made the DICOM format so popular for medical imaging. Nevertheless, this popularity had led to the multiplication of tag definitions, and consequently, it is sometimes difficult to know which tags are used, and what they mean, making the extraction of header information more difficult. DICOM tags may include meta information that provide information associated with the medical image such as, details of the patient, the modality manufacturer, clinical findings, and the like. In certain embodiments, the DICOM tags may also contain the image acquisition protocol. Sometimes, the DICOM header does not contain the image acquisition protocol as it is an optional tag. This becomes are problem when multiple series of images of a particular imaging protocol needs to compared for analysis. If the DICOM header does not contain the image acquisition protocol, the medical personnel have to manually search for the images. This procedure consumes a lot of time and effort. Therefore, there is a need for an easier method to recognize the image acquisition protocol of image sets. Further, there is also a need for comparing two (2) image sets with the same protocol for analysis, without relying on the DICOM tag for referring to the image acquisition protocol.

SUMMARY AND DESCRIPTION

The scope of the present disclosure is defined solely by the appended claims and is not affected to any degree by the statements within this summary. The present embodiments may obviate one or more of the drawbacks or limitations in the related art.

Accordingly, it is an object of the disclosure to provide a method and device for performing automatic detection of medical image acquisition protocol. The method and device makes use of image analysis and statistical algorithms for automatically detecting the image acquisition protocol of a medical image.

An object of the disclosure is achieved by providing a method of automatically detecting medical imaging protocol. The method includes determining, by a processor, anatomy under consideration from a set of Magnetic Resonance (MR) images using landmark detection algorithms. Further, the method includes automatically identifying image acquisition protocol associated with the set of medical images based on the determined anatomy. Further, medical images acquired with the identified image acquisition protocol are identified at different time instances from a medical image database. Finally, a comparative view of the medical images is provided on a display unit for analysis.

In an embodiment, an act of automatically identifying protocol associated with acquisition of the set of medical images based on the determined anatomy includes determining at least one feature associated with the medical images characterizing the acquisition protocol. Further, the medical images are assigned with an image acquisition protocol label, wherein the acquisition protocol label is assigned based on a classification of the medical images.

In another embodiment, classifying the medical images includes detecting an outlier image acquisition protocol based on the at least one feature. Thereafter, the medical images are classified into at least one image acquisition protocol based on the features.

In certain embodiments, the identified image acquisition protocol of the set of medical images is displayed on the display unit.

In certain other embodiments, a plurality of set of medical images of similar image acquisition protocols is displayed adjacent to one another.

In certain embodiments, the method of automatically identifying protocol associated with acquisition of the set of medical images based on the determined anatomy includes determining at least one feature associated with the medical images characterizing the acquisition protocol. Further, the medical images are classified based in the at least one feature. Thereafter, the medical images are assigned with an acquisition protocol label based on the classification of the medical images.

In certain embodiments, the feature includes a two-dimensional Local Binary Pattern (LBP), a 3 dimensional LBP, and saliency weighted Histogram of the LBP.

In certain embodiments, the method of classifying the medical images includes detecting an outlier image acquisition protocol based on the at least one feature. Further, the medical images are classified into at least one image acquisition protocol based on the features.

In certain embodiments, the method of detecting the outlier image acquisition protocol includes determining an error value associated with the features of the medical image. Further, the error value is compared against a threshold value to determine if the image acquisition protocol is an outlier. Thereafter, a result that indicates the image acquisition protocol of the medical image is an outlier is displayed.

In certain embodiments, classification of the medical images is performed using at least one of a probabilistic and a non-probabilistic classifier.

In certain other embodiments, the outlier detection is performed using statistical transformation algorithms.

Another object of the disclosure is to provide a device to automatically detect the image acquisition protocol of a set of medical images. The device includes a processor and a memory that includes processor executable instructions configured for automatically detecting an image acquisition protocol of a medical image.

The above mentioned and other features of the disclosure will now be addressed with reference to the accompanying drawings of the present disclosure. The illustrated embodiments are intended to illustrated, but not limit the disclosure.

BRIEF DESCRIPTION OF THE DRAWINGS

The present disclosure is further described hereinafter with reference to illustrated embodiments shown in the accompanying drawings, in which.

DETAILED DESCRIPTION

Figure 1:
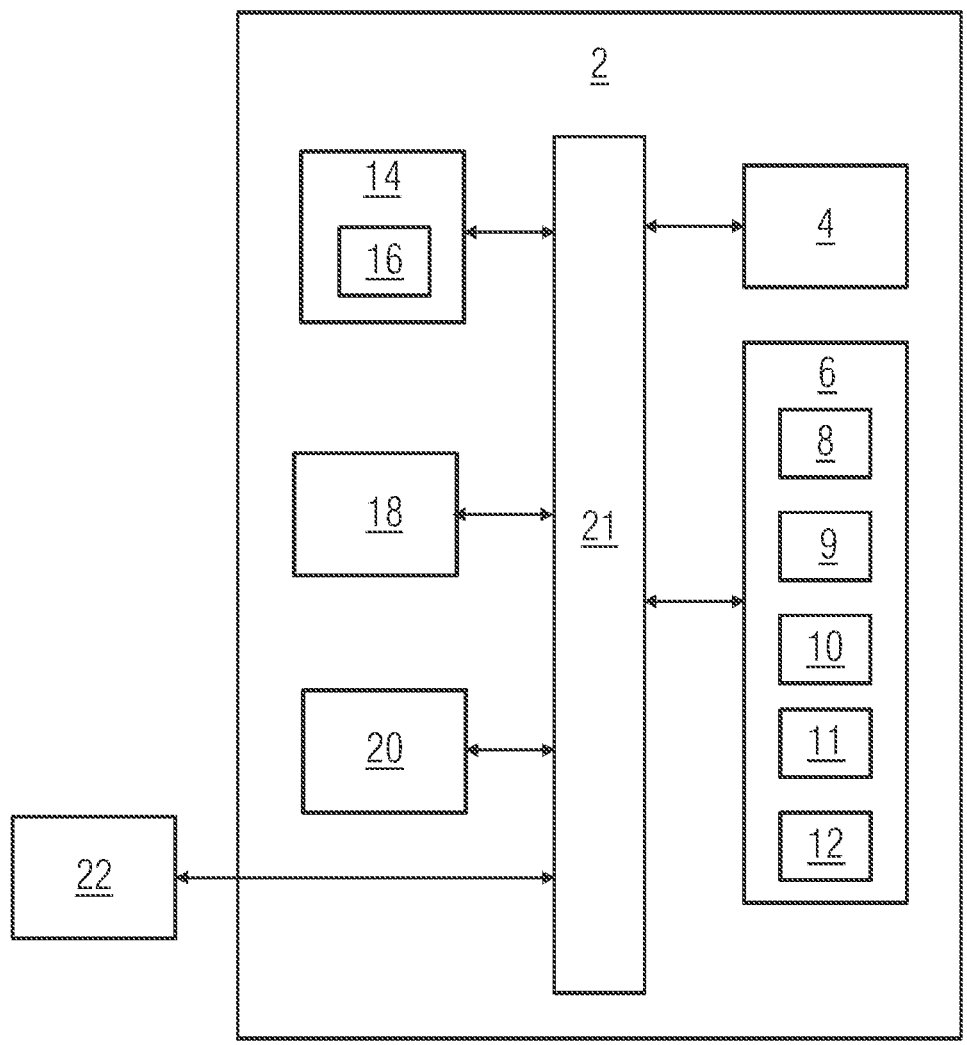
FIG. 1 illustrates a computing device for evaluating medical imaging devices, in accordance with an embodiment.

Various embodiments are described with reference to the drawings, wherein like reference numerals are used to refer like elements throughout. In the following description, for the purpose of explanation, numerous specific details are set forth in order to provide thorough understanding of one or more embodiments. It may be evident that such embodiments may be practiced without these specific details.

FIG. 1 illustrates a computing device for evaluating medical imaging devices, in accordance with an embodiment. FIG. 1 illustrates an exemplary block diagram 1 of the computing device 2 for generating electronic medical records, in accordance with an embodiment. The computing device 2 includes a processor 4, a memory 6, a storage unit 14, an input/output (I/O) unit 18, and a communication module 20. The computing device 2 is also communicatively coupled to a medical imaging device 22. The medical imaging device 22 may include, but is not limited to, a Magnetic Resonance Imaging (MRI) device, a Computerized Tomography (CT) imaging device, and the like. The aforementioned components are connected to each other by a bus unit 21. The processor 4, as used herein, refers to any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, or any other type of processing circuit. The processor 4 may also include embedded controllers, such as generic or programmable logic devices or arrays, application specific integrated circuits, single-chip computers, and the like.

The memory or non-transitory computer readable medium 6 may be volatile memory and non-volatile memory. A variety of computer-readable storage media may be stored in and accessed from the memory 6. The memory 6 may include any suitable elements for storing data and machine-readable instructions, such as read only memory, random access memory, erasable programmable read only memory, electrically erasable programmable read only memory, hard drive, removable media drive for handling compact disks, digital video disks, diskettes, magnetic tape cartridges, memory cards, and the like. As depicted, the memory 6 includes one or more modules for generating medical reports with pre-defined protocol names, according to one or more embodiments described above. The memory 6 includes an anatomy detection module 8, a feature extraction module 9, a statistical classifier module 10, an outlier protocol detection module 11 and label assignment module 12. The anatomy detection module 8 includes computer readable instructions for identifying an anatomy of human body part, in the medical image, using landmark detection algorithms, for example, ALPHA. The medical image may include one or more slices of an anatomy of a subject as captured by a CT or MR modality. Thereafter, the feature extraction module 9 is configured for extracting one or more features from the set of medical images. The features that are extracted may be, for example, two-dimensional Local Binary Patterns (2D LBP), three-dimensional Local Binary Patterns (3D LBP), and Histogram of saliency weighted local binary (HSWLBP) patterns. However, a person skilled in the art may be able to appreciate that the feature extraction module 9 may extract any other features such as, but not limited to filter based features from the medical images. The features may be computed by determining a salient region in a volume of the medical image. Further, the salient regions in the volume of the medical image may be determined by applying a blurring filter and then assigning a saliency value for the pixels above a mean intensity value. In this manner, a very low intensity pixel is assigned a high saliency value highlighting the salient regions in the medical image. Furthermore, the Local binary patterns are computed by known methods for a particular radius and sample size. For example, the LBP may be computed for a radius of 1 and sample size 8. Further, the features extraction module 9 is configured to extract histogram of saliency weighted lower binary patterns (HSWLBP). The HSWLBP is computed by developing a 256 dimensional histogram of the combined LBP of all the slices of an anatomy. The aforementioned features are used to classify the medical images into an image acquisition protocol from a group of several image acquisition protocols.

Further, the memory 6 includes the outlier protocol detection module 11, which is configured to detect if the medical image does not belong to a set of known image acquisition protocols. The outlier protocol detection module 11 determines if the medical image is of an outlier protocol by using a novelty detection algorithm. Initially, an error value associated with the medical image in the context of a reconstruction of the medical image in one of the known set of protocols is determined. In case the error is greater than a threshold value, then the image acquisition protocol of the medical image is concluded to be an outlier protocol. In other words, the image acquisition protocol of the medical image does not belong to the known set of image acquisition protocol. Further, the memory 6 includes the statistical classifier module 10, which classifies the medical image into one of the image acquisition protocol from a group of image acquisition protocol. The statistical classifier module 10 may determine the image acquisition protocol of the medical image based on the features extracted by the feature extraction module 9. The statistical classifier module 10 may be configured to perform the classification by using machine learning algorithms such as random forests and support vector machines. Further, the statistical classifier module 10 may be trained using existing medical images of the known protocol set.

The storage unit 14 may be a non-transitory storage medium configured for storing medical image data 16 including medical images acquired in various imaging protocols. The images data 16 in the storage unit may be used to train the statistical classifier module 10.

The input output module 18 may include a keyboard, keypad, touch sensitive display screen, mouse, and the like. The input/output devices 18 enable the user to interact with the device 2 for controlling the operating state. For example, a display unit may display a screen including one or more graphical objects indicating the image acquisition protocol of the medical image that is considered for analysis.

The device 2 further includes a communication module 20 for communicating with other devices via a network connection. The communication module 20 may include a Wi-Fi transceiver, a network interface card (NIC), and the like.

Figure 2:
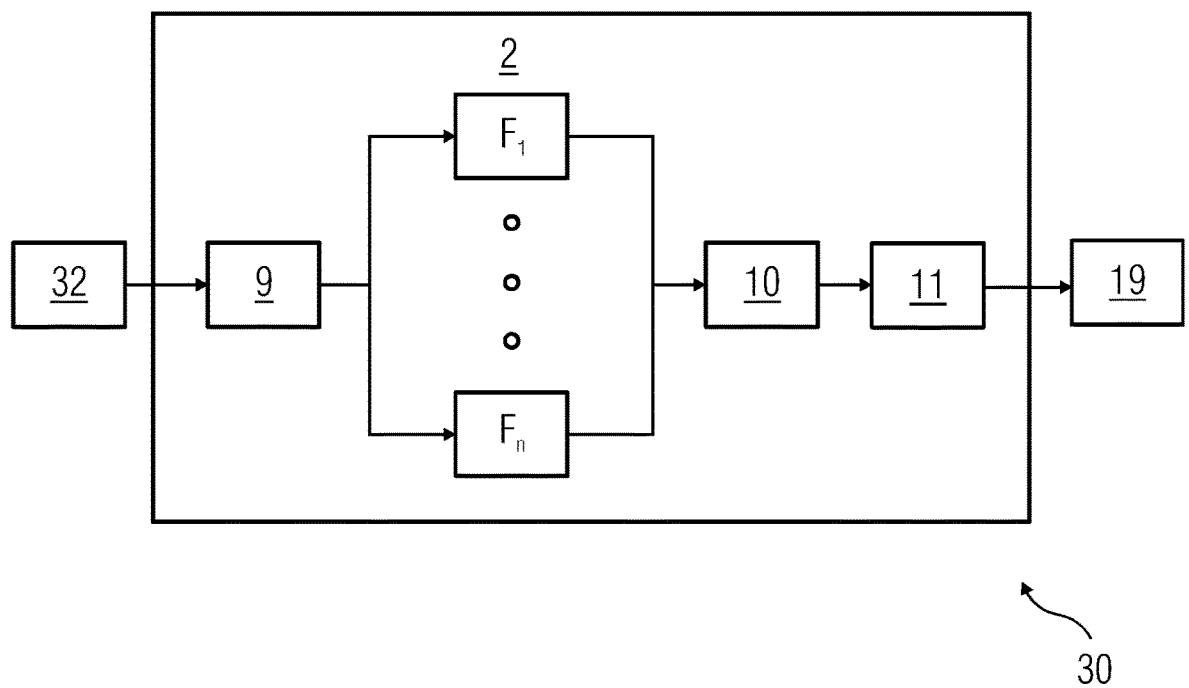
FIG. 2 illustrates a block diagram of the workings of the feature extraction module, outlier detection module, and a classification module, in accordance with an embodiment.

FIG. 2 illustrates an exemplary block diagram of the working of the feature extraction module 9, in accordance with an embodiment. As shown in FIG. 2, the feature extraction module 9 receives a medical image from a source. The source of the medical image may be the image data 16 stored in the storage unit 14. In another embodiment, the medical image 32 may be acquired directly from the imaging modality 22. Further, the feature extraction module 9 is configured to extract one or more features ($F_1, F_2 \ldots F_N$) from the medical image 32. The features may include two-dimensional (2D) and three-dimensional (3D) lower binary patters (LBPs). Furthermore, the features ($F_1, F_2 \ldots F_N$) include Histogram of Saliency Weighted LBPs (HSWLBP). In an embodiment, the 2D and 3D LBPs may be determined by the feature extraction module 9 by using known algorithms for determining LBPs of images. In an exemplary implementation, a Gaussian filter is applied to a volume in the medical image 32 using 3D Gaussian kernel with variance equal to one. Thereafter, all the voxels in blurred version of volume are assigned saliency of 1 if the intensity value of the voxels are above mean intensity value of the whole volume and zero (0) otherwise. The features computed by the feature extraction module 9 are used to determine the image acquisition protocol of the medical image 32. Further, the feature extraction module 9 may be configured to extract any other feature that helps in the determination of the image acquisition protocol. Further the features generated by the feature extraction module 9 are passed on to the statistical classifier module 11 and the outlier protocol detection module 10.

As shown in FIG. 2, features generated by the feature extraction module 9 are received by the outlier protocol detection module 10. The outlier protocol detection module 10 is configured to process the features ($F_1, F_2 \ldots F_N$) to determine if the medical image 32 is generated using an unknown protocol. The outlier protocol detection module 10 may be configured to implement a novelty detection algorithm for determining an outlier protocol. The outlier protocol detection module 10 may make use of a Kernel-Principle Component Analysis (PCA) algorithm for determining an error value associated with the reconstruction of the features of the medical image in a known feature space. In case the error value exceeds a threshold value then the image acquisition protocol used for acquiring the medical image 32 is determined to be an outlier. In one embodiment, if the image acquisition protocol used for acquiring the medical image 32 belongs to one of the known protocol classes being modelled using kernel-PCA then the reconstruction error will be low and vice-versa. Further, a threshold may be determined empirically to classify the sample as an outlier, for which the reconstruction error is above the threshold. In case the outlier protocol detection module 10 determines that the protocol used for acquiring the medical image 32 is an outlier protocol the medical image 32 is discarded and there is no further processing of the same.

Reverting to FIG. 2, in case the outlier protocol detection module 10 provides a positive result regarding the image acquisition protocol for the medical image 32, then the features ($F_1, F_2 \ldots F_N$) are received by the statistical classifier module 11. The statistical classifier module 11 processes the features ($F_1, F_2 \ldots F_N$) characterizing different image acquisition protocols. The features ($F_1, F_2 \ldots F_N$) are selected such that the classes of image acquisition protocols are linearly separable. The statistical classifier module 11 may be configured to Support Vector Machine (SVM) algorithm with linear kernel to provide a good classification of the imaging protocols. Further, the statistical classifier module 11 may make use of other classification algorithms such as Random Forests for classification of the imaging protocols. Furthermore, the statistical classifier module 11 may be trained using a training image data for learning the characteristics of the features of different imaging protocols.

Figure 3:
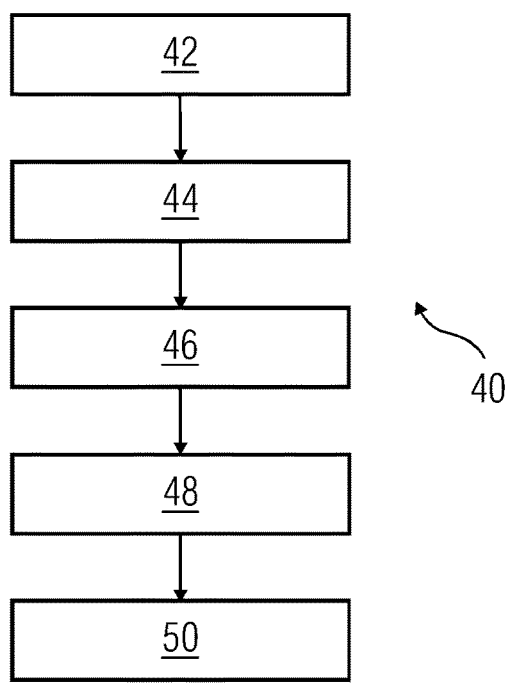
FIG. 3 illustrates a flowchart of a method involving automatically detecting the image acquisition protocol, in accordance with an embodiment.

FIG. 3 illustrates a flowchart 50 of a method involving automatically detecting the image acquisition protocol, in accordance with one or more embodiments. At act 52, anatomy of a medical image is detected. In an embodiment, the anatomy may be detected using landmark detection algorithms such as, but not limited to, ALPHA. At act 54, an image acquisition protocol associated with acquisition of the set of medical images is determined based on the anatomy. In some embodiments, the method of automatically identifying protocol associated with acquisition of the set of medical images based on the determined anatomy includes determining at least one feature associated with the medical images characterizing the acquisition protocol. In some embodiments, the feature includes a two-dimensional Local Binary Pattern (LBP), a three-dimensional LBP and saliency weighted Histogram of the LBP.

In some embodiments, the method of classifying the medical images includes detecting an outlier image acquisition protocol based on the at least one feature. Further, the medical images are classified into at least one image acquisition protocol based on the features. In some embodiments, the method of detecting the outlier image acquisition protocol includes determining an error value associated with the features of the medical image. Further, the error value is compared against a threshold value to determine if the image acquisition protocol is an outlier. Thereafter, a result that indicates the image acquisition protocol of the medical image is an outlier is displayed. In some other embodiments, the outlier detection is performed using statistical transformation algorithms.

At act 56, the medical images are classified based in the at least one feature. Thereafter, the medical images are assigned with an acquisition protocol label based on the classification of the medical images. In some embodiments, classification of the medical images is performed using at least one of a probabilistic and a non-probabilistic classifier algorithm.

At act 58, images acquired with the identified protocol at different time instances from a medical image database are labelled and displayed. In some other embodiments, a plurality of medical images of similar image acquisition protocols is displayed adjacent to one another.

While the present disclosure has been described in detail with reference to certain embodiments, it should be appreciated that the present disclosure is not limited to those embodiments. In view of the present disclosure, many modifications and variations would be present themselves, to those skilled in the art without departing from the scope of the various embodiments of the present disclosure, as described herein. The scope of the present disclosure is, therefore, indicated by the following claims rather than by the foregoing description. All changes, modifications, and variations coming within the meaning and range of equivalency of the claims are to be considered within their scope.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method of automatically detecting a medical imaging protocol, the method comprising:
   receiving, by a processor, a set of medical images from at least one imaging device, the processor being separate from the at least one imaging device;
   determining, by the processor, an anatomy of a body part in at least one medical image from the set of medical images;
   extracting, by the processor, at least one feature associated with the at least one medical image;
   detecting, by the processor, the at least one medical image as an outlier image based on the at least one feature that does not belong to a set of known image acquisition protocols;
   automatically classifying, by the processor, the outlier image into at least one image acquisition protocol based on the at least one feature; and
   identifying medical images acquired with the image acquisition protocol at different time instances from a medical image database.

2. The method of claim 1, further comprising:
   displaying the image acquisition protocol of the set of medical images on a display unit; and
   providing a comparative view of the identified medical images acquired with the image acquisition protocol on the display unit for analysis.

3. The method of claim 1, further comprising:
   assigning the at least one medical image with an image acquisition protocol label based on the classification of the at least one medical image.

4. The method of claim 1, wherein the at least one feature comprises a two-dimensional Local Binary Pattern (LBP), a three-dimensional LBP, and saliency weighted Histogram of the LBP.

5. The method of claim 1, wherein the detecting of the at least one medical image as the outlier image comprises:
   determining an error value associated with the at least one feature of the at least one medical image;
   comparing the error value against a threshold value to determine when the at least one medical image is an outlier; and
   displaying a result indicating the at least one medical image is an outlier.

6. The method of claim 1, wherein the classification of the at least one medical image is performed using a probabilistic classifier and a non-probabilistic classifier.

7. The method of claim 1, wherein the detecting of the outlier image is performed using at least one statistical transformation algorithm.

8. The method of claim 1, wherein the anatomy of the at least one medical image is detected based on at least one landmark detection algorithm.

9. A device for automatically detecting a medical imaging protocol, the device comprising:
   a processor;
   a memory coupled with the processor, wherein the memory comprises processor executable instructions configured to:
   receive at least one medical image from an imaging device, wherein the imaging device is separate from the device;
   determine an anatomy of a body part in the at least one medical image from a set of medical images;
   extract at least one feature associated with the at least one medical image;
   detect the at least one medical image as an outlier image based on the at least one feature that does not belong to a set of known image acquisition protocols;
   automatically classify the outlier image into at least one image acquisition protocol based on the at least one feature; and
   identify medical images acquired with the image acquisition protocol at different time instances from a medical image database.

10. The device of claim 9, further comprising:
    a display unit,
    wherein the processor executable instructions are further configured to:
    display the image acquisition protocol of the set of medical images on the display unit; and
    provide a comparative view of the identified medical images acquired with the image acquisition protocol on a display unit for analysis.

11. The device of claim 9, wherein the processor executable instructions further comprise instructions configured to:
    assign the identified medical images with an acquisition protocol label, wherein the acquisition protocol label is assigned based on the classification of the identified medical images.

12. The device of claim 9, wherein the processor executable instructions configured for detecting the outlier image comprise instructions configured to:

determine an error value in a reconstruction feature space of a medical image of the identified medical images; and label the medical image as an outlier based on the error value as compared with a threshold value.

13. The device of claim 9, wherein the device is configured to receive magnetic resonance images from the imaging device.

14. The device of claim 9, wherein the processor executable instructions are configured to use at least one of a probabilistic and a non-probabilistic classifier to classify the identified medical images.

15. The device of claim 12, wherein the processor executable instructions are configured to use at least one statistical transformation algorithm to detect the outlier image.

16. The device of claim 9, wherein the anatomy of the at least one medical image is detected based on landmark detection algorithms.

\* \* \* \* \*